(12) United States Patent
Moon et al.

(10) Patent No.: US 6,262,083 B1
(45) Date of Patent: Jul. 17, 2001

(54) GENIPIN DERIVATIVE HAVING LIVER PROTECTION ACTIVITY

(75) Inventors: Sung-Hwan Moon; Hea-Jin Choi; Su-Jin Lee; Jea-Uk Chung; Jong-Ryul Ha; Kyoung-June Lee; Se-Woong Oh; Kwang-Won Jeong, all of Kyunggi-do (KR)

(73) Assignee: Choongwae Pharma Corporation, Seoul (KR)

( * ) Notice: Subject to any disclaimer, the term of this patent is extended or adjusted under 35 U.S.C. 154(b) by 0 days.

(21) Appl. No.: 09/530,796

(22) PCT Filed: Sep. 4, 1998

(86) PCT No.: PCT/KR98/00273

§ 371 Date: May 5, 2000

§ 102(e) Date: May 5, 2000

(87) PCT Pub. No.: WO99/23090

PCT Pub. Date: May 14, 1999

(30) Foreign Application Priority Data

Nov. 5, 1997 (KR) .................................................. 97-58131
Dec. 5, 1997 (KR) .................................................. 97-66389
Dec. 10, 1997 (KR) ................................................. 97-67407

(51) Int. Cl.[7] ........................... C07D 311/94; A61K 31/35

(52) U.S. Cl. .................... 514/337; 546/283.4; 546/283.7; 546/284.1; 549/387; 549/396; 514/463; 514/469; 514/338

(58) Field of Search ............................. 546/283.4, 283.7, 546/284.1; 549/387, 396; 514/387, 463, 469, 338

(56) References Cited

FOREIGN PATENT DOCUMENTS

A1 4323567   1/1994   (DE) .
   066682  *  3/1991   (JP) .................................... 546/283.4
A1 9817663   4/1998   (WO) .

OTHER PUBLICATIONS

Bentley et al., Chem. Abstracts Citation of J. Chem. Soc. C, vol. 21, pp. 2234–2240, 1967.*

* cited by examiner

Primary Examiner—Zinna Northington Davis
(74) Attorney, Agent, or Firm—Birch, Stewart, Kolasch & Birch, LLP

(57) ABSTRACT

The present invention relates to novel genipin derivatives which have an excellent liver protection activity with little cytotoxicity, and these compounds are so stable in vivo that they do not induce any side effects.

11 Claims, No Drawings

GENIPIN DERIVATIVE HAVING LIVER PROTECTION ACTIVITY

This application is the national phase under 35 U.S.C. § 371 of PCT International Application No. PCT/KR98/00273 which has an International filing date of Sep. 4, 1998, which designated the United States of America.

TECHNICAL FIELD

The present invention relates to novel genipin derivatives represented by the following formulas (I)a, (I)b, (I)c and (I)d, which have a liver protection activity:

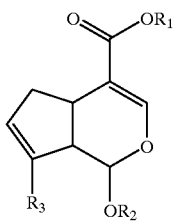

(I)a in which $R_1$ represents lower alkyl;

$R_2$ represents lower alkyl, pyridylcarbonyl, benzyl or benzoyl;

$R_3$ represents formyl, hydroxymethyl, azidomethyl, 1-hydroxyethyl, acetyl, methyl, hydroxy, pyridylcarbonyl, cyclopropyl, aminomethyl substituted or unsubstituted by (1,3-benzodioxolan-5-yl)carbonyl or 3,4,5-trimethoxybenzoyl, 1,3-benzodioxolan-5-yl, ureidomethyl substituted or unsubstituted by 3,4,5-trimethoxyphenyl or 2-chloro-6-methyl-3-pyridyl, thiomethyl substituted or unsubstituted by acetyl or 2-acetylamino-2-ethoxycarbonylethyl, oxymethyl substituted or unsubstituted by benzoyl, pyridylcarbonyl or 3,4,5-trimethoxybenzoyl;

provided that $R_3$ is not formyl, hydroxymethyl, acetyl, methylaminomethyl, acetylthiomethyl, benzoyloxymethyl or pyridylcarbonyloxymethyl when $R_1$ is methyl.

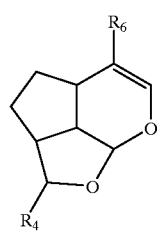

(I)b in which $R_4$ represents lower alkoxy, benzyloxy, benzoyloxy, phenylthio, $C_1$~$C_{12}$ alkanoyloxy substituted or unsubstituted by t-butyl, phenyl, phenoxy, pyridyl or thienyl;

$R_5$ represents methoxycarbonyl, formyl, hydroxyiminomethyl, methoxyiminomethyl, hydroxymethyl, phenylthiomethyl or acetylthiomethyl;

provided that $R_5$ is not methoxycarbonyl when $R_4$ is acetyloxy.

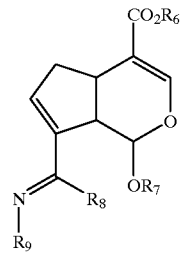

(I)c in which $R_6$ represents hydrogen atom, lower alkyl or alkalimetal;

$R_7$ represents lower alkyl or benzyl;

$R_8$ represents hydrogen atom or lower alkyl;

$R_9$ represents hydroxy, lower alkoxy, benzyloxy, nicotinoyloxy, isonicotinoyloxy, 2-pyridylmethoxy or hydroxycarbonylmethoxy;

provided that $R_9$ is not hydroxy or methoxy when $R_6$ is methyl and $R_8$ is hydrogen atom.

(I)d in which $R_{10}$ represents lower alkyl;

$R_{11}$ represents lower alkyl or benzyl;

$R_{12}$ represents lower alkyl, pyridyl substituted or unsubstituted by halogen, pyridylamino substituted or unsubstituted by lower alkyl or halogen, 1,3-benzodioxolanyl;

$R_{13}$ and $R_{14}$ each independently represent a hydrogen atom or join together to form isopropylidene together; and their pharmaceutically acceptable salts, or stereoisomers.

The present invention also relates to pharmaceutical compositions comprising as an active ingredient of the compound of formulas (I)a, (I)b, (I)c and (I)d, which can be effectively used for the liver protection activity.

BACKGROUND ART

It has been reported that the known iridoids genipin represented by the following formula (A) and aucubin represented by the following formula (B) are natural substances, and act as a therapeutic agent for hepatitis B through the mechanism to inhibit the HBV replication (see, Korean Patent Laid-open No. 94-1886).

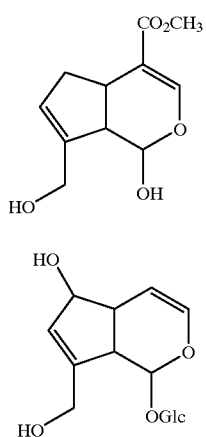

(A)

(B)

Said genipin of formula (A) and aucubin of formula (B) have some in vivo activities such as liver-protection, inhibition of biosynthesis of RNA and protein, detoxification as well as antiviral activity. Particularly, it has been disclosed that genipin is also effective as an anti-tumor agent (Japanese Patent Laid-open No. 80/164625). However, these compounds may be decomposed with amino acid residues of proteins such as albumin. Such a series of reactions may induce some color change of urine, faeces, and various internal organs into blue as well as immunotoxicities.

Compounds having a similar structure to the compound according to the present invention include the compound represented by the following formula (C) in addition to genipin and aucubin (see, WO 92/06061 and European Patent Laid-open No. EP-0505572):

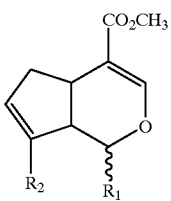

(C)

in which
R₁ represents benzyloxyl, hydroxy, acetoxy or ethoxyethoxy, and
R₂ represents benzoyloxymethyl, methoxymethyl, t-butyldimethylsilyloxymethyl, carboxy or hydroxymethyl.

It is described in the above literatures that the compound of formula (C) above may be used effectively as a therapeutic agent for hyperlipemia or as a cholagogues.

On the other hand, the present inventors have synthesized a series of novel aucubin and genipin derivatives on the basis of the prior arts as mentioned above in order to develop compounds having a superior activity to the earlier compounds on inhibition against HBV. After the antiviral activity and little cytotoxicity of the novel compounds prepared were identified, the present inventors have filed a patent application on the novel compounds (see, Korean Patent Laid-open No. 97-21072).

DISCLOSURE OF INVENTION

The present inventors have continuously and intensively studied to develop novel compounds having more improved properties, and as a result, have succeeded to synthesize new compounds of formulas (I)a, (I)b, (I)c and (I)d according to the present invention. By determining the antiviral activity and cytotoxicity of the compounds, we have identified that compounds according to the present invention are so stable in vivo that they do not induce any side effects such as change to blue color, etc. and that they may be effectively used for liver protection since they have an excellent liver protection activity with little cytotoxicity.

Therefore, it is an object of the present invention to provide novel genipin derivatives represented by the following formulas (I)a, (I)b, (I)c and (I)d which have an excellent liver protection activity as well as little cytotoxicity:

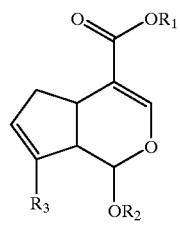

(I)a in which
$R_1$ represents lower alkyl;
$R_2$ represents lower alkyl, pyridylcarbonyl, benzyl or benzoyl;
$R_3$ represents formyl, hydroxymethyl, azidomethyl, 1-hydroxyethyl, acetyl, methyl, hydroxy, pyridylcarbonyl, cyclopropyl, aminomethyl substituted or unsubstituted by (1,3-benzodioxolan-5-yl)carbonyl or 3,4,5-trimethoxybenzoyl, 1,3-benzodioxolan-5-yl, ureidomethyl substituted or unsubstituted by 3,4,5-trimethoxyphenyl or 2-chloro-6-methyl-3-pyridyl, thiomethyl substituted or unsubstituted by acetyl or 2-acetylamino-2-ethoxycarbonylethyl, oxymethyl substituted or unsubstituted by benzoyl, pyridylcarbonyl or 3,4,5-trimethoxybenzoyl;
provided that $R_3$ is not formyl, hydroxymethyl, acetyl, methylaminomethyl, acetylthiomethyl, benzoyloxymethyl or pyridylcarbonyloxymethyl when $R_1$ is methyl.

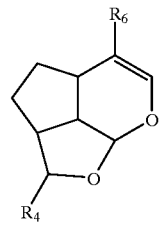

(I)b in which
$R_4$ represents lower alkoxy, benzyloxy, benzoyloxy, phenylthio, $C_1$~$C_{12}$ alkanoyloxy substituted or unsubstituted by t-butyl, phenyl, phenoxy, pyridyl or thienyl;
$R_5$ represents methoxycarbonyl, formyl, hydroxyiminomethyl, methoxyiminomethyl, hydroxymethyl, phenylthiomethyl or acetylthiomethyl;
provided that $R_5$ is not methoxycarbonyl when $R_4$ is acetyloxy.

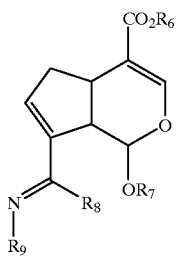

(I)c in which
- $R_6$ represents hydrogen atom, lower alkyl or alkalimetal;
- $R_7$ represents lower alkyl or benzyl;
- $R_8$ represents hydrogen atom or lower alkyl;
- $R_9$ represents hydroxy, lower alkoxy, benzyloxy, nicotinoyloxy, isonicotinoyloxy, 2-pyridylmethoxy or hydroxycarbonylmethoxy;
- provided that $R_9$ is not hydroxy or methoxy when $R_6$ is methyl and $R_8$ is hydrogen atom.

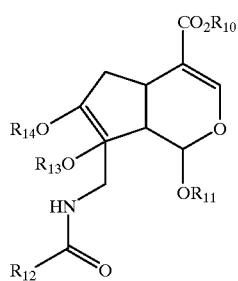

(I)d in which
- $R_{10}$ represents lower alkyl;
- $R_{11}$ represents lower alkyl or benzyl;
- $R_{12}$ represents lower alkyl, pyridyl substituted or unsubstituted by halogen, pyridylamino substituted or unsubstituted by lower alkyl or halogen, 1,3-benzodioxolanyl;
- $R_{13}$ and $R_{14}$ each independently represent a hydrogen atom or join together to form isopropylidene.

And their pharmaceutically acceptable salts or stereoisomers.

It is another object of the present invention to provide pharmaceutical compositions for the liver protection comprising as active ingredients the compound of formulas (I)a, (I)b, (I)c and (I)d as defined above, together with pharmaceutically acceptable inert carriers.

BEST MODE FOR CARRYING OUT THE INVENTION

Among the compounds of formula (I)a having a potent liver protection activity, the preferred compounds include those wherein $R_1$ represents methyl, $R_2$ represents benzyl or methyl and $R_3$ represents 1-hydroxyethyl, aminomethyl, 3,4,5-trimethoxy benzoylaminomethyl, N-hydroxy-N-methylaminomethyl or 3,4,5-trimethoxyphenylureidomethyl.

Among the compounds of formula (I)b having a potent liver protection activity, the preferred compounds include those wherein $R_4$ represents acetyloxy when $R_5$ is acetylthiomethyl, formyl, hydroxyiminomethyl or methoxyiminomethyl; $R_4$ represents acetylthio when $R_5$ is methoxycarbonyl, acetylthiomethyl, formyl or methoxyiminomethyl; $R_4$ represents t-butylacetyloxy when $R_5$ is methoxycarbonyl, acetylthiomethyl or formyl; $R_4$ represents isonicotinoyloxy when $R_5$ is methoxycarbonyl or acetylthiomethyl; $R_4$ represents benzyloxy, phenylthio, pivaloyloxy, lauroyloxy, phenylacetyloxy, hydrosynamoyloxy, phenoxyacetyloxy, thiophenacetyloxy or benzoyloxy when $R_5$ is methoxycarbonyl.

Among the compounds of formula (I)c having a potent liver protection activity, the preferred compounds include those wherein $R_6$ represents hydrogen atom, methyl, isopropyl or sodium, $R_7$ represents methyl or benzyl, $R_8$ represents hydrogen atom or methyl, and $R_9$ represents hydroxy, methoxy, t-buthoxy, benzyloxy, nicotinoyloxy, isonicotinoyloxy, 2-pyridylmethoxy or hydroxycarbonylmethoxy.

Among the compounds of formula (I)d having a potent liver protection activity, the preferred compounds include those wherein $R_{10}$ represents methyl, $R_{11}$ represents methyl or benzyl, $R_{12}$ represents 3-pyridyl, 2-chloro-6-methyl-3-pyridyl, 3-pyridylamino, 2-chloro-3-pyridylamino, 2-chloro-6-methyl-3-pyridylamino, 5,6-dichloro-3-pyridylamino or 1,3-benzodioxolan-5-yl and $R_{13}$ and $R_{14}$ each independently represent a hydrogen atom or join together to form isopropylidene.

The compounds of formulas (I)a, (I)b, (I)c and (I)d according to the present invention can form pharmaceutically acceptable salts. Such salts include a salt with pharmaceutically acceptable acids such as asparagic acid, gluconic acid, glutamic acid, hydrochloric acid, p-toluenesulfonic acid or citric acid, etc., and a salt with acids or bases which are generally known and conventionally used in the technical field of iridoid-based compounds. These pharmaceutically acceptable salts can be prepared according to a conventional conversion method.

Synthetic Process for Preparing Compounds

The compounds of formulas (I)a, (I)b, (I)c and (I)d of the present invention can be prepared according to the methods described below. However, it should be understood that the process for preparing compounds of formulas (I)a, (I)b, (I)c and (I)d are not limited to those explained below since the compound can be easily prepared by optionally combining the various methods disclosed in prior arts, and such a combination may be conventionally carried out by a person having ordinary skill in the art.

Following is reaction scheme of preparing the compound of formula (I)a.

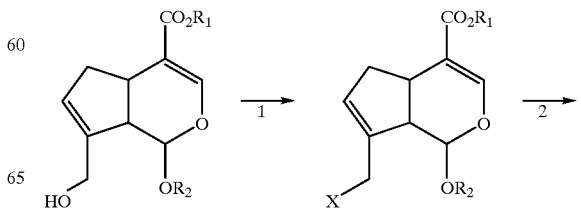

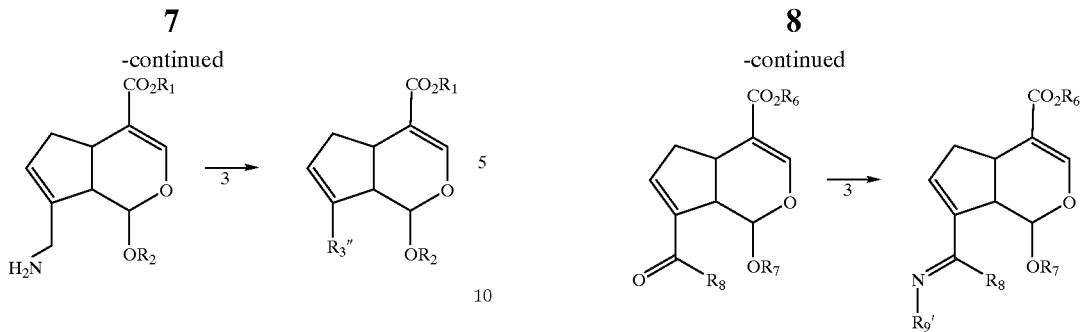

The definitions of $R_1$~$R_3$ are same as described above.

Following is reaction scheme of preparing the compound of formula (I)b.

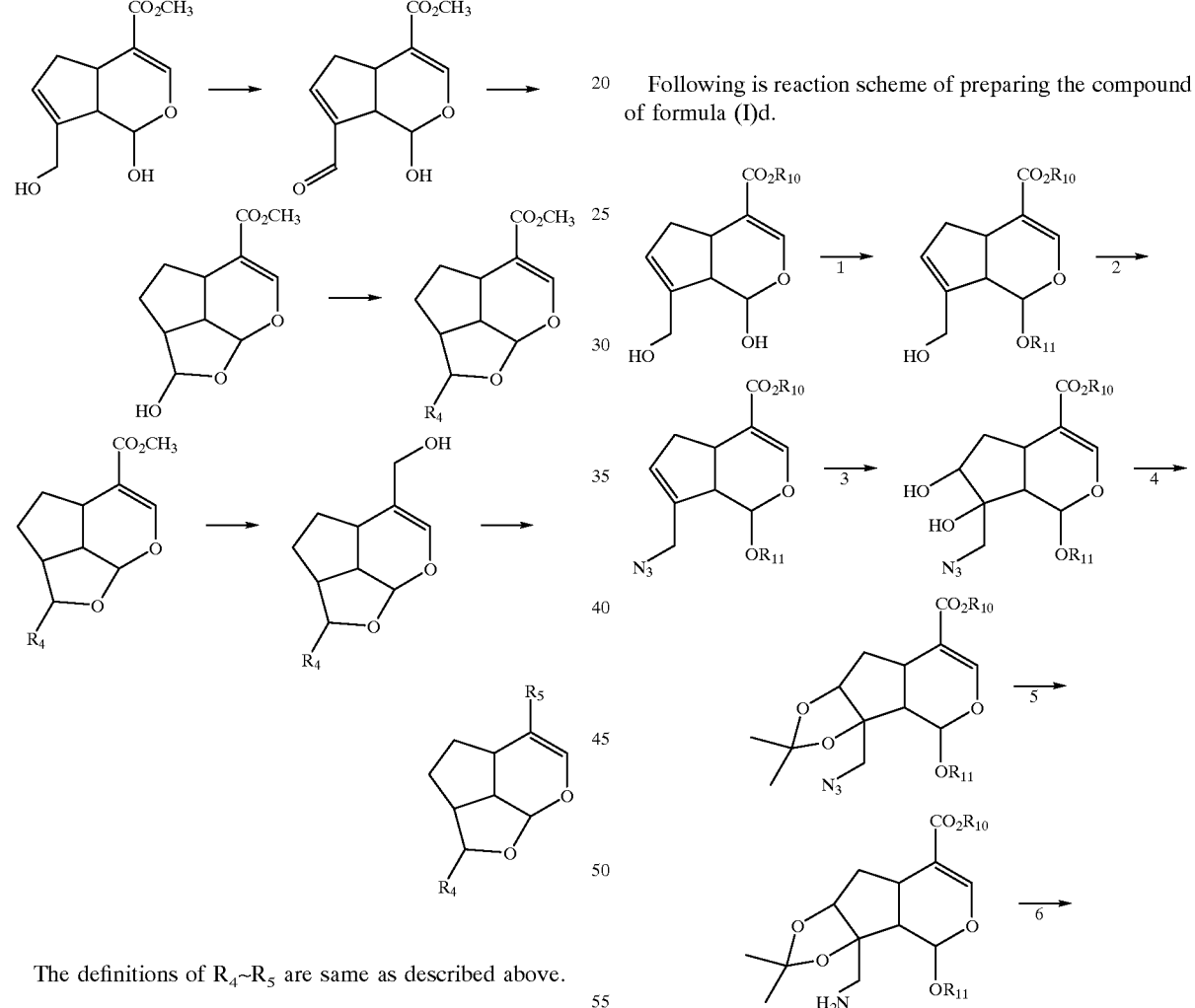

The definitions of $R_4$~$R_5$ are same as described above.

Following is reaction scheme of preparing the compound of formula (I)c.

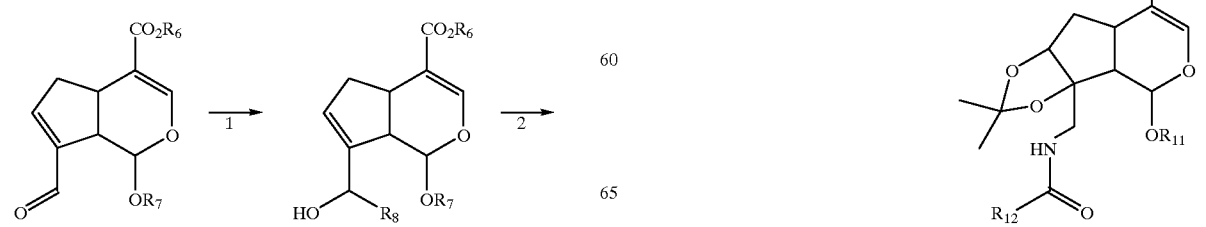

The definitions of $R_6$~$R_9$ are same as described above.

Following is reaction scheme of preparing the compound of formula (I)d.

-continued

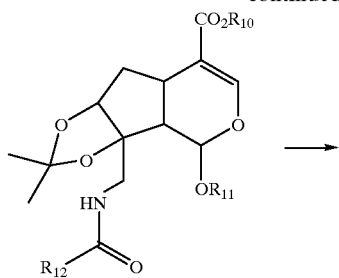

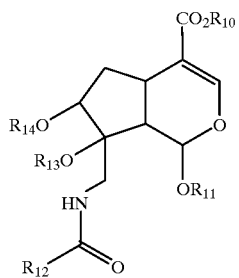

The definitions of $R_{10}$~$R_{14}$ are same as described above.

Efficacy and Toxicity of Compounds of Formulas (I)a, (I)b, (I)c and (I)d

The efficacy of compounds of formulas (I)a, (I)b, (I)c and (I)d was measured according to the method of carbon tetrachloride model [referred to: Philippe letteron et al., *Biochemical Pharmacology*, 39, 12, 2027~2034, 1990] and D-galactosamine model [referred to: Koji Hase et al., *Biol. Pharm. Bull.*, 20, 4, 381~385, 1997].

Carbon tetrachloride and D-galactosamine are known as the compounds inducing the severe damage to liver cells, because carbon tetrachloride suppresses the biosysthesis of protein in the liver and induces the necrosis of liver cells, and D-galactosamine also induces the necrosis of liver cells by changing the structure of liver cell membranes.

In the present invention, the compounds of formulas (I)a, (I)b, (I)c and (I)d were orally administered to the rats as experimental animals for 4 days, and then the liver protection effect was examined by measuring the serum ALT or AST values in the experimental animals (referred to: *Biol. Prarm. Bull.*, 20, 4, 38 1~385, 1997; *Toxicology and Applied Pharmacology*, 95, 1~11, 1988).

Following is calculation formula to evaluate liver protection properties of compounds of formulas (I)a, (I)b, (I)c and (I)d;

$$\left[1 - \frac{ALT \text{ value of the group administered by the compounds} - ALT \text{ value of normal group}}{ALT \text{ value of control group} - ALT \text{ value of normal group}}\right] \times 100$$

in above formula
the control group means the group to which carbon tetrachloride or D-galactosamine is administered and the liver cells are impaired;
the normal group means the group to which normal solution is administered.

The liver protection effects of compounds of formulas (I)a, (I)b, (I)c and (I)d are shown to following Table 1 in comparison with known liver protection compound silimarin.

TABLE 1

| Administration compounds | Dose (mg/kg) | Route | Liver protection effect (GPT, %) |
|---|---|---|---|
| Silimarin | 100 | i.p | 74 |
| Silimarin | 100 | p.o | 50 |
| Compound (I)a | 100 | p.o | 65 |
| Compound (I)b | 100 | p.o | 57 |
| Compound (I)c | 100 | p.o | 64 |
| Compound (I)d | 100 | p.o | 74 |

※ The compound (I)a represents methyl (7R,3aS,7aS)-1-azidomethyl-7-benzyloxy-3,7,3a,7a-tetrahydro-6-oxaindene-4-carboxylate prepared in example 1.

The compound (I)b represents (2S,2aR,4aS,7aR,7bS)-2-methoxy-5-methoxycarbonyl-2a,3,4,4a,7a,7b-hexahydro-2H-1,7-dioxacyclopent[c.d]indene prepared in example 3.

The compound (I)c represents methyl (1S,5R,6S)-5-benzyloxy-7-(t-buthoxyiminomethyl)-4-oxa-bicyclo[4.3.0]nona-2,7-dien-2-carboxylate prepared in example 4.

The compound (I)d represents methyl (1S,8S,12S)-2-[(3-pyridyl)ureido]methyl-4,4-dimethyl-3,5,11-trioxa-12-benzyloxy-tricyclo[6.4.0.0<2,6>]dodec-9-en-9-carboxylate prepared in example 7.

On the other hand, the acute toxicity of compounds of formulas (I)a, (I)b, (I)c and (I)d is measured using mouse according to the standard of drug toxicity test. The mouse is selected from the 4 weeks old ICR mouse and each dosage of 250 mg/kg, 500 mg/kg, 1,000 mg/kg and 2,000 mg/kg compounds of formulas (I)a, (I)b, (I)c and (I)d are administered after suspending the compounds in the corn oil. Table 2 shows the acute toxicity of the compounds of formulas (I)a, (I)b, (I)c and (I)d.

TABLE 2

| Administration compounds | Dosage(mg/kg) | Number of dead animals/Number of administered animals | Lethal ratio (%) |
|---|---|---|---|
| Compound (I)a | 250 | 0/5 | 0 |
|  | 500 | 015 | 0 |
|  | 1000 | 0/5 | 0 |
|  | 2000 | 0/5 | 0 |
| Compound (I)b | 250 | 0/5 | 0 |
|  | 500 | 0/5 | 0 |
|  | 1000 | 0/5 | 0 |
|  | 2000 | 0/5 | 0 |
| Compound (I)c | 250 | 0/5 | 0 |
|  | 500 | 0/5 | 0 |
|  | 1000 | 0/5 | 0 |
|  | 2000 | 0/5 | 0 |
| Compound (I)d | 250 | 0/5 | 0 |
|  | 500 | 0/5 | 0 |
|  | 1000 | 0/5 | 0 |
|  | 2000 | 0/5 | 0 |

Therefore, the compounds of formulas (I)a, (I)b, (I)c and (I)d are proved as very safe materials. Further, the inventors have performed cytotoxicity text using the neutral red dye uptake method to determine. As a result, it was identified that the toxicity of compounds of formulas (I)a, (I)b, (I)c and (I)d is much less than that of dideoxy cytidine. Also, from the acute toxicity test using mouse as the test animal, it could be seen that the compound according to the present invention has a superior safety to the known compound genipin.

Consequently, compounds of formulas (I)a, (I)b, (I)c and (I)d according to the present invention are safe and have an excellent therapeutic effect for liver protection. Therefore, it is another object of the present invention to provide pharmaceutical compositions for the liver protection comprising as active ingredients of compounds of formulas (I)a, (I)b, (I)c and (I)d, as defined above, or their pharmaceutically acceptable salts.

When the pharmaceutical compositions according to the present invention are used for clinical purpose, they may be formulated into solid, semi-solid or liquid pharmaceutical preparations for oral or paranteral administration by combining compounds of formulas (I)a, (I)b, (I)c and (I)d with pharmaceutically acceptable inert carriers.

The pharmaceutically acceptable inert carriers which can be used for this purpose may be solid or liquid. It may be one or more selected from the group consisting of diluents, flavouring agents, solubilizing agents, lubricants, suspending agents, binders, swelling agents, etc. Specific example of the solid or liquid carrier which may be suitably used in the present invention includes lactose, starch, mannitol, cottonseed oil, etc.

When the active compounds of formulas (I)a, (I)b, (I)c and (I)d of the present invention are used as medicine for the prevention or protection of the liver, it is preferably administered in an amount of 0.1 to 100 mg per kg of body weight per day at the first stage. However, the administration dosage can be varied with the requirement of the subject patient, severity of the infections to be treated, the selected compound and the like. The preferred dosage suitable for a certain condition can be determined by a person skilled in this art according to a conventional manner. In general, the therapeutic treatment is started from the amount less than the optimal dosage of the active compound and then the administration dosage is increased little by little until the optimal therapeutic effect is obtained. As a matter of convenience, the total daily dosage can be divided into several portions and administered over several times.

The present invention will be more specifically explained by the following examples. However, it should be understood that the examples are intended to illustrate but not in any manner to limit the scope of the present invention.

EXAMPLE 1

Synthesis of Methyl (b 7R,3aS,7aS)-1-azidomethyl-7-benzyloxy-3,7,3a,7a-tetrahydro-6-oxaindene-4-carboxylate (I)a

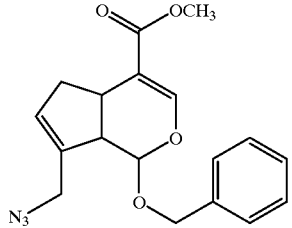

Methyl (7R,3aS, 7aS)-1-hydroxymethyl-7-benzyloxy-3,7,3a,7a-tetrahydro-6-oxa-indene-4-carboxylate (3.66 g, 0.012 mol) was dissolved with 50 ml of methylene-chloride, and cooled to 0° C. under nitrogen atmosphere. Triethylamine (8.1 ml, 0.058 mol) was added drop by drop to the reaction mixture, and stirred for 30 min. Again, methansulfonylchloride (2.7 ml, 0.035 mol) was added and the reaction was finished after a lapse of 30 min. Saturated sodiumbicarbonate solution was added to finish the reaction, and the organic solvent layer was separated and washed by normal saline, then, dried, filtered and concentrated with anhydrous magnesium sulfate. The residue was dissolved with 10 ml of DMF and sodiumazide (2.26 g, 0.035 mol) was added and stirred at 50° C. for one night. After confirmation of the reaction by TLC, ethylacetate/hexane (1:2, v/v) and saturated saline were added to the reaction mixture. In the organic layer, the material was dried, filtered and concentrated, and the captioned compound was obtained by column chromatography (eluant:hexane/ethylacetate=1/10, v/v Rf=0.25). White solid phase of captioned compound was obtained (3.16 g; yield 80%).

$^1$H NMR (300 MHz, CDCl$_3$):

δ 2.14 (m, 1H), 2.70 (t, 1H, J=7.2 Hz), 2.94 (dd, 1H, J=8.5, 16.8 Hz), 3.28 (dd, 1H, J=8.1, 16.5 Hz), 3.76 (s, 3H), 3.89 (d, 1H, J=14.7 Hz), 4.00 (d, 1H, J=14.7 Hz), 4.66 (d, 1H, J=11.4 Hz), 4.70 (d, 1H, J=8.0 Hz), 4.99 (d, 1H, J=11.6 Hz), 5.91 (s, 2H), 7.37 (m, 5H), 7.72 (s, 1H).

EXAMPLE 2

Synthesis of Methyl (b 7R,3aS,7aS)-1-aminomethyl-7-benzyloxy-3,7,3a,7a-tetrahydro-6-oxaindene-4-carboxylate (I)a

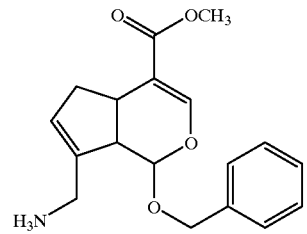

The compound obtained in example 1 (0.557 g, 1.63 mmol) was dissolved with 5 ml of methaol and trichloride 1 hydrate (0.773 g, 4.08 mmol) was added. After stirring for 2 hours, the completion of the reaction was confirmed and the solvent was evaporated. Ethylacetate and water were added to the residue, and cooled at 0° C., then sodium hydroxide added to separate the layers. After separating the organic layer, saturated saline was added to wash the layer several times and dried, filtered and concentrated with anhydrous sodium sulfate. The concentrated solution was purified by silica gel column chromatography (eluant:methanol/chloroform/triethylamine=1/10/0.1, v/v/v, Rf=0.3). Yellow solid phase of captioned compound was obtained (0.411 g; yield 80%).

$^1$H NMR (300 MHz, CDCl$_3$):

δ 2.13 (m, 1H), 2.70 (t, 1H, J=7.2 Hz), 2.90 (dd, 1H, J=8.5, 16.8 Hz), 3.25 (dd, 1H, J=8.1, 16.5 Hz), 3.76 (s, 3H), 3.89 (d, 1H, J=14.7 Hz), 4.10 (d, 1H, J=14.7 Hz), 4.26 (d, 1H, J=12.4 Hz), 4.70 (d, 1H, J=8.0 Hz), 4.59 (d, 1H, J=12.6 Hz), 5.91 (s, 2H), 7.37 (m, 5H), 7.72 (s, 1H)

EXAMPLE 3

Synthesis of (2S,2aR,4aS,7aR,7bS)-2-methoxy-5-methoxycarbonyl-2a,3,4,4a,7a,7b-hexa-hydro-2H-1,7-dioxacyclopent[c.d]indene (I)b

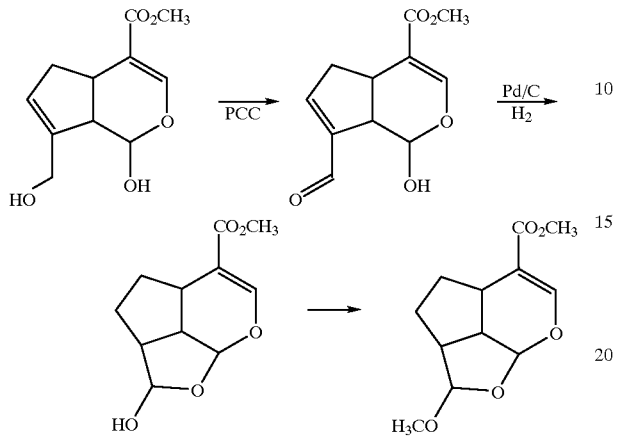

10 g (44.2 mmol) of methyl(4aS,7aS)-1-hydroxy-7-hydroxymethyl-1,4a,5,7a-tetra hydrocyclopenta[c]pyrane-4-carboxylate was dissolved with 600 ml of methylene chloride, and 19.06 g (88.4 mmol) of pyridiniumchlorocromate was added, and stirred for 2 hours. After filtering the reaction mixture, the filtered solution was concentrated and purified by using column chromatography (hexane/ethylacetate=3/1, v/v), and 8.78 g of methyl(4aS,7aS)-7-formyl-1-hydroxy-1,4a,5,7a-tetra hydrocyclopenta[c]pyrane-4-carboxylate was obtained (yield: 89%).

10 g (44.6 mmol) of obtained compound was dissolved with 300 ml of ethanol, and 10% Pd/C (0.5 g) was added in room temparature, and stirred for 1 hour in hydrogen atmosphere (1 atm). The reaction mixture was filtered and concentrated in reduced pressure. Concentrated residue was purified by using column chromatography (hexane/ethylacetate=4/1, v/v), and 6.5 g of white solid phase of methyl(2S,2aR,4aS,7aR,7bS)-2-hydroxy-2a,3,4,4a,7a,7b-hexahydro-2H-1,7-dioxacyclopent[c,d]indene-carboxylate was obtained (yield: 60%).

2.3 g (10.17 mmol) of obtained compound was dissolved with 60 ml of anhydro methaol and cooled to 0° C. 2.3 ml of trifluoroborondiethylether (48%) was added and stirred for 2 hours in room temperature. The reaction mixture was cooled to 0° C. and neutralized with saturated sodiumbicarbonate solution, and organic solvent was removed in reduced pressure. After extracting the water layer with ethylacetate twice, the extracted solution was washed with saturated saline and dried and concentrated with anhydrosodiumsulfate. Residue was purified by using column chromatography (hexane/ethylacetate=4/1, v/v), and 2.1 g of oil phase of captioned compound was obtained (yield: 86%).

¹H NMR (CDCl₃);

δ 1.01–1.13 (m, 1H), 1.69 (m, 1H), 1.85 (m, 1H), 2.26 (m, 2H), 2.54–2.75 (m, 1H), 3.38 (s, 3H), 3.71 (s, 3H), 4.56 (d, 1H, J=1.28 Hz), 5.73 (d, 1H, J=4.83 Hz) 7.53 (s, 1H)

¹³C NMR (CDCl₃);

25.99, 30.01, 33.85, 39.73, 51.59, 51.68, 55.60, 99.78, 109.58, 110.51, 150.16, 168.18

EXAMPLE 4

Synthesis of Methyl (1S,5R,6S)-5-benzyloxy-7-(t-buthoxyiminomethyl)-4-oxa-bicyclo [4.3.0]nona-2,7-dien-2-carboxylate (I)c

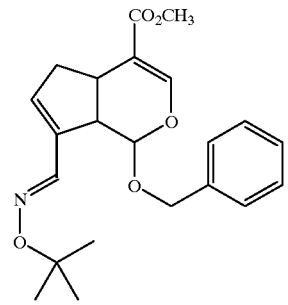

Methyl (1S,5R,6S)-5-benzyloxy-7-(t-buthoxyiminomethyl)-4-oxa-bicyclo[4.3.0]nona-2,7-dien-2-carboxylate (0.63 g, 2.00 mmol) was dissolved in 11 ml of mixed solution of methanol and water (10/1, v/v), and 0.34 g of t-buthoxylamine hydrochloride (2.71 mmol) was added and stirred for 1 hour in room temperature, and reaction mixture was concentrated. Residue was dissolved with ethylacetate, and washed with saturated saline solution, and dried, filtered and concentrated with anhydrous magnesium sulfate. Residue was purified by using silica gel column chromatography (hexane/ethylacetate=10/1, v/v), and 0.64 g of white solid phase of captioned compound was obtained (yield: 83%).

¹H NMR (300 MHz, CDCl₃);

δ 1.19 (s, 9H), 2.37–2.45 (m, 1H), 2.82–2.92 (m, 1H), 3.38–3.40 (m, 2H), 3.75 (s, 3H), 4.63 (d, 1H, J=12.3 Hz), 4.83 (d, 1H, J=12.3 Hz), 5.70 (d, 1H, J=2.6 Hz), 6.06 (s, 1H), 7.29–7.37 (m, 5H), 7.50 (s, 1H), 7.83 (s, 1H)

¹³C NMR (CDCl₃);

δ 27.84, 33.09, 39.34, 47.54, 51.51, 70.53, 79.13, 97.04, 112.04, 128.19, 128.26, 128.83, 136.79, 137.65, 138.21, 145.09, 152.33, 168.11

MASS: 386 [M+1]⁺

EXAMPLE 5

Synthesis of Methyl (1S,5R,6S)-5-benzyloxy-7-benzyloxyiminomethyl-4-oxa-bicyclo [4.3.0]nona-2,7-dien-2-carboxylate (I)c

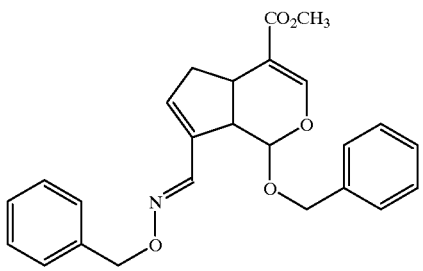

The process was carried out in the same manners of the example 4 except that benzyloxyamine hydrochloride was used instead of t-buthoxylamine hydrochloride (yield: 83%).

¹H NMR (300 MHz, CDCl₃);

δ 2.36–2.43 (m, 1H), 2.86–2.94 (m, 1H), 3.34–3.39 (m, 2H), 3.76 (s, 3H), 4.60 (d, 1H, J=12.1 Hz), 4.84 (d, 1H,

J=12.1 Hz), 5.03 (s, 2H), 5.53 (d, 1H, J=3.9 Hz), 6.15 (s, 1H), 7.29–7.40 (m, 5H), 7.52 (s, 1H), 7.94 (s, 1H)

$^{13}$C NMR (CDCl$_3$);

δ 33.52, 39.61, 47.08, 51.51, 70.79, 76.61, 97.72, 111.77, 128.16, 128.23, 128.29, 128.38, 128.76, 136.26, 137.68, 137.92, 139.61, 146.61, 152.44, 168.06

MASS: 420 [M+1]$^+$, 442 [M+23]$^+$

EXAMPLE 6

Synthesis of Methyl (1S,5R,6S)-5-benzyloxy-7-hydroxycarbonylmethoxyiminomethyl-4-oxa-bicyclo[4.3.0]nona-2,7-dien-2-carboxylate (I)c

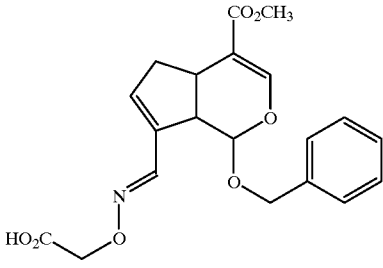

The process was carried out in the same manners of the example 4 except that hydroxycarbonylmethoxylamine hydrochloride was used instead of t-buthoxylamine hydrochloride (yield: 44%).

$^1$H NMR (300 MHz, CDCl$_3$);

δ 2.31–2.39 (m, 1H), 2.86–2.95 (m, 1H), 3.23–3.27 (m, 1H), 3.31–3.36 (m, 1H), 3.75 (s, 3H), 4.55 (s, 2H), 4.62 (d, 1H, J=12.1 Hz), 4.86 (d, 1H, J=12.1 Hz), 5.34 (d, 1H, J=4.8 Hz), 6.23 (bs, 1H), 7.29–7.36 (m, 5H), 7.52 (s, 1H), 7.98 (s, 1H)

$^{13}$C NMR (75 MHz, CDCl$_3$)

δ 33.94, 39.75, 51.65, 70.56, 70.79, 97.65, 111.49, 128.31, 128.39, 128.77, 128.91, 135.72, 137.35, 141.57, 148.23, 152.63, 168.11, 174.75

MASS: 388 [M+1]$^+$, 410 [M+23]$^+$

EXAMPLE 7

Synthesis of Methyl (1S,8S,12S)-2-[(3-pyridyl)ureido]methyl-4,4-dimethyl-3,5,11-trioxa-12-benzyloxy-tricyclo[6.4.0.0<2,6>]dodec-9-en-9-carboxylate (I)d

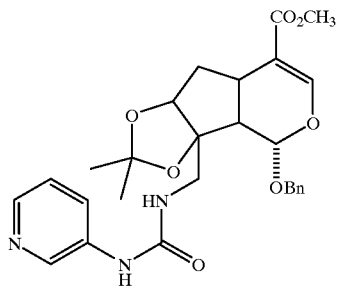

Nicotinic acid hydrochloride (296 mg, 2.40 mmol) was suspended with 2 ml of methylene chloride and 2 ml of oxalic chloride was added and refluxed with stirring for 3 hours, then concentrated in reduced pressure. Residue was suspended with 10 ml of toluene and sodiumazide (468 mg, 7.2 mmol) was added and refluxed with stirring for 1 night to form 3-pyridylisocyanate. Methyl (1S,8S,12S)-2-aminomethyl-4,4-dimethyl-3,5,11-trioxa-12-benzyloxy-tricyclo[6.4.0.0<2,6>] dodec-9-en-9-carboxylate was added to above obtaind solution, and 2 ml of pyridine was added drop by drop and stirred for 2 hours at room temperature. Ethylacetate was added to reaction mixture and washed with saturated sodium bicarbonate and saturated saline solution. After drying and concentrating with anhydrous magnesium sulfate, residue was purified by using silica gel column chromatography (hexane/ethylacetate=2/1, v/v), and 550 mg of captioned compound was obtained (yield: 90%).

$^1$H NMR (300 MHz, CDCl$_3$);

δ 1.27 (s, 3H), 1.37 (s, 3H), 1.98 (m, 1H), 2.10 (m, 1H), 2.10 (m, 1H), 2.39 (m, 1H), 3.09 (m, 1H), 3.20 (d, 1H, J=13.4 Hz), 3.67 (s, 3H), 4.05 (dd, 1H, J=9.8, 14.2 Hz), 4.29 (d, 1H, J=7.1 Hz), 4.56 (d, 1H, J=11.2 Hz), 4.69 (d, 1H, J=11.2 Hz), 5.42 (d, 1H, J=3.4 Hz), 5.55 (d, 1H, J=9.3 Hz), 7.21 (m, 6H), 7.34 (s, 1H), 7.72 (s, 1H), 8.06 (d, 1H, J=8.4 Hz), 8.19 (brs, 1H), 8.35 (brs, 1H)

EXAMPLE 8

Synthesis of Methyl (1S,8S,12R)-2-[(5,6-dichloro-3-pyridyl)ureido]methyl-4,4-dimethyl-3,5,11-trioxa-12-benzyloxy-tricyclo[6.4.0.0<2,6>]dodec-9-en-9-carboxylate (I)d

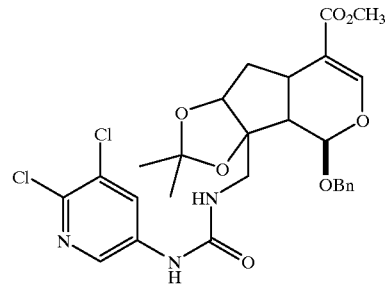

The process was carried out in the same manners of the example 7 except that 5,6-dichloronicotinic acid hydrochloride (691 mg, 3.6 mmol) was used instead of nicotinic acid hydrochloride, and methyl (1S,8S,12R)-2-aminomethyl-4,4-dimethyl-3,5,11-trioxa-12-benzyloxy-tricyclo[6.4.0.0<2,6>] dodec-9-en-9-carboxylate (467 mg, 1.2 mmol) was used instead of methyl (1S,8S,12S)-2-aminomethyl-4,4-dimethyl-3,5,11-trioxa-12-benzyloxy-tricyclo[6.4.0.0<2,6>] dodec-9-en-9-carboxylateand. The captioned compound was obtained (yield: 40%).

$^1$H NMR (300 MHz, CDCl$_3$);

δ 1.36 (s, 1H), 1.46 (2s, 6H), 2.28 (m, 1H), 2.48 (dd, 1H, J=6.2, 14.2 Hz), 3.05 (m, 1H), 3.39 (m, 1H), 3.76 (s, 3H), 4.12 (m, 1H), 4.40 (d, 1H, J=5.1 Hz), 4.55 (d, 1H, J=10.3 Hz), 4.79 (d, 1H, J=9.4 Hz), 5.13 (d, 1H, J=10.3 Hz), 5.38 (d, 1H, J=6.7 Hz), 5.6 (bs, 1H), 7.40 (m, 5H), 7.52 (s, 1H), 7.83 (d, 1H, J=2.5 Hz), 8.20 (d, 1H, J=2.5 Hz)

EXAMPLE 9

Synthesis of Methyl (1S,8S,12R)-2-[(2-chloro-3-pyridyl)ureido]methyl-4,4-dimethyl-3,5,11-trioxa-12-methoxy-tricyclo[6.4.0.0<2,6>]dodec-9-en-9-carboxylate (I)d

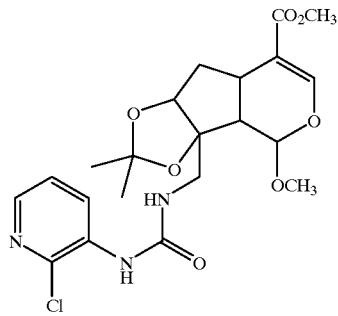

Genipin (5 g, 22.1 mmol) was dissolved with 250 ml of methanol and catalytic amount of trifluoroboron diethylether was added, and stirred for 3 hours, then saturated sodium bicarbonate solution was added to finish the reaction. Under reduce pressure, methanol was removed and extracted with ethylacetate, and dried, filtered and concentrated with anhydous magnesium sulfate. Oily phase of methyl (3aS,7aS)-1-hydroxymethyl-7-methoxy-3,7,3a,7a-tetrahydro-6-oxaindene-4-carboxylate (5.26 g, 7S:7R=1:3) was obtained.

The process was carried out in the same manners of the example 7 using obtained compound as starting material except that 2-chloronicotinic acid hydrochloride (567 mg, 3.6 mmol) was used instead of nicotinic acid hydrochloride (yield: 85%).

$^1$H NMR (300 MHz, CDCl$_3$)

δ 1.43 (s, 3H), 1.48 (m, 1H), 1.49 (s, 3H), 2.31 (m, 1H), 2.50 (dd, 1H, J=6.8, 14.5 Hz), 3.33 (m, 2H), 3.58 (s, 3H), 3.75 (s, 3H), 3.90 (m, 1H), 4.43 (d, 1H, J=5.1 Hz), 4.59 (d, 1H, J=8.7 Hz), 5.71 (d, 1H, J=4.3 Hz), 7.10 (bs, 1H), 7.22 (m, 1H), 7.51 (s, 1H), 8.01 (dd, 1H, J=1.6, 4.6 Hz), 8.53 (dd, 1H, J=1.6, 8.2 Hz)

EXAMPLE 10

Inhibitory Effect on HBV Replication

Test for identifying the anti HBV effect of the compound of the present invention was carried out according to a known assay method (see, Korba and Milman, Antiviral Res., 15, 217, 1991). The assay procedure is briefly described in the following.

A. Cell culture 2.2.15. cell was cultured and preserved in RPM 11640 culture medium containing 5% fetal bovine serum (FBS), 2 mM glutamine and 50 μg/ml gentamicin sulfate. Resistance to G418 of the cell culture and degree of Mycoplasma contamination were examined according to conventional methods.

Cells (1×10$^4$/cm$^2$) were inoculated into a multi-well tissue culture plate, confluently cultured for 7 days, and then kept for 2 or 3 days in confluent condition to stabilize the HBV DNA level. Then, culture medium was replaced 24 hours before cells were exposed to test compound. During the treatment of 9 days, culture medium was replaced and then test compound was added to the fresh culture medium at intervals of 24 hours. Culture medium was collected immediately before the first introduction of test compound, and after 3, 6, 9 days, respectively, and stored at −70° C. before HBV DNA analysis. Then, cytolysis was carried out to analyze the intracellular HBV DNA.

B. Extraction of DNA and RNA

To analyze the extracellular HBV DNA, 0.2 ml of culture medium was incubated in 1M NaOH/10×SSC (1×SSC= 0.15M NaCl/0.015M sodium citrate, pH 7.2) for 20 minutes at 25° C. and then immediately applied to a nitrocellulose membrane presoaked in 20×SSC using a slot blot apparatus. The sample was washed twice with 0.5 ml of 1M Tris/2M NaCl (pH 7.2) and once with 0.5 ml of 20×SSC to neutralize, and then it was washed again with 2×SSC and heated at 8° C. for one hour under vacuum. Generally, the cells which have been cultured and preserved in a dish having a diameter of 10 cm are dissolved in 6 ml of lysis buffer, and the extracellular DNA is prepared according to the method of Korba et al., 1991.

C. Elctrophoresis in gel

10 μg/lane of cellular DNA sample was digested with restriction enzyme Hind III. Then, the digested sample was applied to 1% agarose gel electrophoresis and transferred to a nitrocellulose membrane.

D. Hybridization analysis of HBV DNA 3.2 kb HBV DNA fragment obtained by EcoR I-digestion and purification was labeled with [$^{32}$P]dCTP using nick translation method. This labeled fragment was used as a hybridization probe. Condition for hybridization and post-washing were controlled by referring to the method of Korba et al., 1991 and HBV nucleic acid content among test sample was determined by Ambis beta scanner. The relative radio-activity of $^{32}$P hybridized to the test sample was compared with that of $^{32}$P hybridized to the standard amount of HBV DNA which was applied to each nitrocellulose membrane filter (gel or slot blot). From the calibration curve, the amount of HBV DNA corresponding to the relative cpm value was calculated.

Since the content of intracellular and extracellular HBV DNA has some inherent variations, only inhibition greater than 3.5-fold in the case of HBV virion DNA or 3.0-fold in the case of HBV DNA replication intermediates form the average level of HBV DNA formed in the untreated cell were considered to be statistically significant (P<0.05) in the present experiment. The lever of HBV DNA integrated during each cellular DNA preparation (which remains constant per cell in the present experiment) was used to calculate the level of intracellular HBV DNA formed, thereby the technical variations inherent in the blot hybridization analysis can be eliminated. Typical values for extracellular HBV virion DNA in the untreated cells ranged from 50 to 150 pg/ml culture medium with an average value of about 75 pg/ml. Intracellular HBV DNA replication intermediates (RI) in the untreated cells ranged form 50 to 100 pg/μg cellular DNA with an average value of about 74 pg/μg. On the basis of the results from the hybridization analysis carried out in the present invention, 1.0 pg of intracellular HBV DNA/μg cellular DNA corresponded to 2 to 3 genome copies per cell, and 1.0 pg of extracellular HBV DNA/ml culture medium corresponded to 3×10$^5$ virus particles.

According to the method as explained above, the inhibitory effect of the compound of the present invention of HBV replication ws evaluated. Herein, untreated group was used as a control and ddC (dideoxy cytidine) known as a potent therapeutic agent for hepatitis as well as AIDS was used as a comparative compound. The anti viral activities of the novel genipin derivatives of formulas (I)a, (I)b, (I)c and (I)d, are described in the following Table 3.

EXAMPLE 11

Cytotoxicity Test

Cytotoxivity test was carried out in order to determine whether the antiviral effect of the compound according to the present invention is due to the general influence on cell growth or not. In the present experiment, neutral red dye uptake method was used. This is a standard method widely utilized for examining cell survival, by which the variety of relations between viruses such as HSV or HIV and host organism can be understood.

Cytotoxicity test was performed on a 96-well tissue culture plate. Cells were cultured and treated with test compounds in the same manner as Biological Example 1, and the experiments at 4-kind concentrations were repeated threetimes, respectively. Since the relative toxicity can be determined form the uptake level of neutral red dye, quantitative analysis was carried out using the absorbance of internalized dye at 510 nm ($A_{510}$). The test results on cytotoxicity are also describeb in the following Table 3.

Table 3.

Inhibitory effect of the compounds of formulas (I)$a$, (I)$b$, (I)$c$ and (I)$d$ on HBV replication in 2.2.15 cell culture, cytotoxivity, and SI (selectivity Index, $IC_{50}/ED_{50}$)

| Compound No. | $ED_{50}$ ($\mu$M) | $IC_{50}$ ($\mu$M) | SI |
| --- | --- | --- | --- |
| (I)a | 80 | 120 | 4.5 |
| (I)b | 40 | 90 | 3.0 |
| (I)c | 30 | 180 | 5.7 |
| (I)d | 20 | 70 | 2.5 |
| ddC | 15 | >30 | >2.0 |

※The compound (I)$a$ represents methyl (7R,3$a$S,7$a$S)-1-azidomethyl7-benzyloxy-3,7,3$a$,7$a$- tetrahydro-6-oxaindene-4-carboxylate prepared in example 1.

The compound (I)$b$ represents (2S,2$a$R,4$a$S,7$a$R,7$b$S)-2-methoxy-5-methoxy-carbonyl-2$a$,3,4,4$a$,7$a$,7$b$-hexahydro-2H-1,7-diosacyclopent[c,d]indene prepared in example 3.

The compound (I)$c$ represents methyl (1s,5R,6S)-5-benzyloxy-7-(t-buthoxy-iminomethyl)-4-oxa-bicyclo[4.3.0]nona-2,7-dien-2-carboxylate prepared in example 4.

The compound (I)$d$ represents methyl (1S,8S,12S)-2-[(3-pyridyl)ureido]methyl-4,4-dimethyl-3,5,11-trioxa-12-benzyloxy-tricyclo[6.4.0.0<2.6>]dodec-9-en-9-carboxylate prepared in example 7.

As can be seen form the results of Table 3, the compounds of formulas (I)$a$, (I)$b$, (I)$c$ and (I)$d$ according to the present invention exhibit a potent inhibitory activity on HBV replication and its safety has been remarkably improved compared with the known compound ddC. Therefore, it is expected that the compound of the present invention can be preferably used in the treatment of hepatitis B.

What is claimed is:

1. A novel genipin compound represented by the following formula (I)$a$ :

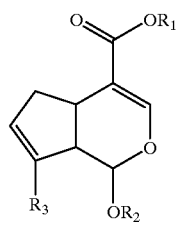

(I)a in which $R_1$ represents lower alkyl;

$R_2$ represents lower alkyl, pyridylcarbonyl, benzyl or benzoyl;

$R_3$ represents formyl, hydroxymethyl, azidomethyl, 1-hydroxyethyl, acetyl, methyl, hydroxy, pyridylcarbonyl, cyclopropyl, aminomethyl substituted or unsubstituted by (1,3-benzodioxolan-5-yl)carbonyl or 3,4,5-trimethoxybenzoyl, 1,3-benzodioxolan-5-yl, ureidomethyl substituted or unsubstituted by 3,4,5-trimethoxyphenyl or 2-chloro-6-methyl-3-pyridyl, thiomethyl substituted or unsubstituted by acetyl or 2-acetylamino2-ethoxycarbonyethyl, oxymethyl substituted or unsubstituted by benzoyl, pyridylcarbonyl or 3,4,5-trimethoxybenzoyl;

provided that $R_3$ is not methyl formyl, hydroxymethyl, acetyl, methylaminomethyl, acetylthiomethyl, benzoyloxymethyl or pyridylcarbonyloxymethyl when $R_1$ is methyl, and its pharaceutically acceptable salts, or stereoisomers.

2. A novel genipin compound represented by the following formula (I)$b$:

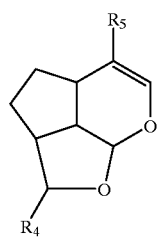

(I)b in which $R_4$ represents lower alkoxy, benzyloxy, benzoyloxy, phenylthio, $C_1$~$C_{12}$ alkanyloxy substituted or unsubstituted by t-butyl, phenyl, phenoxy, pyridyl or thienyl;

$R_5$ represents methoxycarbonyl, formyl, hydroxyiminomethyl, methoxyimino-methyl, hydroxymethyl, phenylthiomethyl or acetylthiomethyl;

provided that $R_5$ is not methoxycarbonyl when $R_4$ is acetyloxy; and its pharmaceutically acceptable salts, or stereoisomers.

3. A novel genipin compound represented by the following formula (I)$c$ :

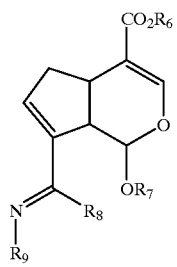

(I)c $R_6$ represents hydrogen atom, lower alkyl or alkalimetal;
$R_7$ represents lower alkyl or benzyl;
$R_8$ represents hydrogen atom or lower alkyl;
$R_9$ represents hydroxy, lower alkoxy, benzyloxy, nicotinoyloxy, isonicotinoyloxy, 2-pyridylmethoxy or hydroxycarbonylmethoxy;
provided that $R_9$ is not hydroxy or methoxy when $R_6$ is methyl and $R_8$ is hydrogen atom; and
its pharmaceutically acceptable salts, or stereoisomers.

4. A novel genipin compound represented by the following formula (I)$d$;

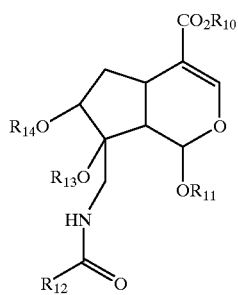

(I)d in which
$R_{10}$ represents lower alkyl;
$R_{11}$ represents lower alkyl or benzyl;
$R_{12}$ represents lower alkyl, pyridyl substituted or unsubstituted by halogen, pyridylamino substituted or unsubstituted by lower alkyl or halogen, 1,3-benzodioxolanyl;
$R_{13}$ and $R_{14}$ each independently represent a hydrogen atom or join together to form isopropylidene; and
its pharmaceutically acceptable salts, or stereoisomers.

5. The compound of claim 1, wherein $R_1$ represents methyl, $R_2$ represents benzyl or methyl and $R_3$ represents 1-hydroxyethyl, aminomethyl, 3,4,5-trimethoxy-benzoylaminomethyl, N-hydroxy-N-methylaminomethyl or 3,4,5-trimethoxy-phenylureidomethyl.

6. The compound of claim 2, wherein $R_4$ represents acetyloxy when $R_5$ is acetylthiomethyl, formyl, hydroxyiminomethyl or methoxyiminomethyl; $R_4$ represents acetylthio when $R_5$ is methoxycarbonyl, acetylthiomethyl, formyl or methoxyiminomethyl; $R_4$ represents t-butylacetyloxy when $R_5$ is methoxycarbonyl, acetylthiomethyl or formyl; $R_4$ represents isonicotinclyoxy when $R_5$ is methoxycarbonyl or acetylthiomethyl; $R_4$ represents benzyloxy, phenylthio, pivaloyloxy, lauroyloxy, phenylacetyloxy, hydrosynamoyloxy, phenoxyacetyloxy, thiophenacetyloxy or benzoyloxy when $R_5$ is methoxycarbonyl.

7. The compound of claim 3, wherein $R_6$ represents hydrogen atom, methyl, isopropyl or sodium, $R_7$ represents methyl or benzyl, $R_8$ represents hydrogen atom or methyl, and $R_9$ represents hydroxy, methoxy, t-butyl, benzyloxy, nicotinoyloxy, isonicotinoyloxy, 2-pyridylmethoxy or hydroxycarbonylmethoxy.

8. The compound of claim 4, wherein $R_{10}$ represents methyl, $R_{11}$ represents methyl or benzyl, $R_{12}$ represents 3-pyridyl, 2-chloro-6-methyl-3-pyridyl, 3-pyridylamino, 2-chloro-3-pyridylamino, 2-chloro-6-methyl-3-pyridylamino, 5,6-dichloro-3-pyridyl-amino or 1,3-benzodioxolan-5-yl and $R_{13}$ and $R_{14}$ each independently represent a hydrogen atom or join together to form isopropylidene.

9. A pharmaceutical composition comprising the compound disclosed in any one of the preceding claims 1 to 8 as an active ingredient together with a pharmaceutically acceptable inert carrier.

10. The pharmaceutical composition of claim 9, wherein the inert carrier is one or more selected from a group consisting of lactose, starch, mannitol and cottonseed oil.

11. A method of treating hepatitis B liver disease, the method comprising:
administering a pharmacologically effective amount of a pharmaceutical composition as recited in claim 9 to a patient in need thereof.

* * * * *